(12) United States Patent
Goddard et al.

(10) Patent No.: US 9,359,587 B2
(45) Date of Patent: Jun. 7, 2016

(54) YEAST STRAINS AND METHODS OF USE THEREOF

(71) Applicants: Matthew Robert Goddard, Waitakere (NZ); Richard Clague Gardner, Epsom (NZ); Nicole Anfang, Auckland (NZ)

(72) Inventors: Matthew Robert Goddard, Waitakere (NZ); Richard Clague Gardner, Epsom (NZ); Nicole Anfang, Auckland (NZ)

(73) Assignee: AUCKLAND UNISERVICES LIMITED, Auckland (NZ)

( * ) Notice: Subject to any disclaimer, the term of this patent is extended or adjusted under 35 U.S.C. 154(b) by 0 days.

(21) Appl. No.: 13/850,925

(22) Filed: Mar. 26, 2013

(65) Prior Publication Data

US 2013/0273197 A1  Oct. 17, 2013

Related U.S. Application Data

(62) Division of application No. 12/921,018, filed as application No. PCT/NZ2009/000029 on Mar. 6, 2009.

(30) Foreign Application Priority Data

Mar. 7, 2008 (NZ) ........................................ 566518

(51) Int. Cl.
| | |
|---|---|
| *C12N 1/00* | (2006.01) |
| *C12G 1/022* | (2006.01) |
| *C12G 1/00* | (2006.01) |
| *C12P 11/00* | (2006.01) |
| *C12P 39/00* | (2006.01) |
| *C12R 1/84* | (2006.01) |

(52) U.S. Cl.
CPC ................ *C12G 1/0203* (2013.01); *C12G 1/00* (2013.01); *C12P 11/00* (2013.01); *C12P 39/00* (2013.01); *C12R 1/84* (2013.01)

(58) Field of Classification Search
CPC ...... C12R 1/84; A23V 2002/00; C12P 39/00; C12P 11/00; C12G 1/00
USPC ............................................................ 426/60
See application file for complete search history.

(56) References Cited

U.S. PATENT DOCUMENTS

| | | | |
|---|---|---|---|
| 4,368,268 A | 1/1983 | Gong | |
| 2007/0292919 A1* | 12/2007 | Holt et al. | .................... 435/69.1 |
| 2009/0163382 A1 | 6/2009 | Oh et al. | |
| 2011/0045140 A1 | 2/2011 | Goddard et al. | |

FOREIGN PATENT DOCUMENTS

AU  20024211444 B2  8/2004

OTHER PUBLICATIONS

Clemente-Jimenez, et al., Influence of Sequential Yeast Mixtures on Wine Fermentation, International Journal of Food Microbiology 98 (2005) 301-308.*

(Continued)

*Primary Examiner* — D. Lawrence Tarazano
*Assistant Examiner* — Philip Dubois
(74) *Attorney, Agent, or Firm* — Foley & Lardner LLP

(57) ABSTRACT

The present invention relates to yeast strains and, in particular, to yeast stains for use in fermentation processes. The invention also relates to methods of fermentation using the yeast strains of the invention either alone or in combination with other yeast strains. The invention thither relates to methods for the selection of yeast strains suitable for fermentation cultures by screening for various metabolic products and the use of specific nutrient sources.

20 Claims, 19 Drawing Sheets

(56) References Cited

OTHER PUBLICATIONS

Egli, Dynamics of indigenous and inoculated yeast populations and their effect on the sensory character of Riesling and Chardonnay wines, Journal of Applied Microbiology 1998, 85, 779-789.*

LEMA, Contribution of Sacharoyces and Non-Saccharomyces Populations to the Prodution of Soe Components of ALBARINO Wine Aroma, Am. J. Enol. Vitiv., vol. 47, No. 2, 1996.*

"Yeast strain combinations influence wine flavours", R & D at Work, Grape and Wine Research and Development Corporation, Australian Government, Jul. 2006, 1 page.

Anfang et al., "Co-fermentation with *Pichia kluyveri* increases varietal thiol concentrations in Sauvignon Blanc", Australian Journal of Grape and Wine Research, 2009, vol. 15, pp. 1-8 (published online 2008).

Dubourdieu et al., "The Role of Yeasts in Grape Flavor Development during Fermentation: The Example of Sauvignon blanc", Am. J. Enol. Vitic., vol. 57, 2006, pp. 81-88.

Final Office Action dated Feb. 18, 2015 issued in U.S. Appl. No. 12/921,018.

Howell et al., Genetic Determinants of Volatile-Thiol Release by *Saccharomyces cerevisiae* during Wine Fermentation, vol. 71, No. 9, Sep. 2005, pp. 5420-5426.

Howell et al., "Metabolic profiling as a tool for revealing *Saccharomyces* interactions during wine fermentation", FEMS Yeast Res., No. 6, Oct. 2005, pp. 91-101.

International Search Report dated Jul. 20, 2009 issued in PCT/NZ2009/000029.

Jespersen et al., "Occurrence and diversity of yeasts involved in fermentation of West African cocoa beans", No. 5, Dec. 2004, pp. 441-453.

Johnson et al., "Population Genetics of the Wild Yeast *Saccharomyces paradoxus*", Genetics, No. 166, Jan. 2004, pp. 43-52.

King et al., "Coinoculated Fermentations Using *Saccharomyces* Yeasts Affect the Volatile Composition and Sensory Properties of *Tiflis vinifera* L. cv. Sauvignon Blanc Wines", Journal of Agricultural and Food Chemistry, 2008, vol. 56, pp. 10829-10837 (published online Oct. 2008).

Kurtzman et al., "Identification and phylogeny of ascomycetous yeasts from analysis of nuclear large subunit (26S) ribosomal DNA partial sequences", Antonie Van Leeuwenhoek, May 1998. vol. 73, pp. 331-371.

Marais and Jolly, Effect of yeast strain and lees contact on Chenin blanc wine quality, Technical Yearbook, Sep. 2005, pp. 85-87.

Office Action dated Oct. 4, 2013 issued in U.S. Appl. No. 12/921,018.

Office Action dated Feb. 28, 2013 issued in U.S. Appl. No. 12/921,018.

Office Action dated Apr. 25, 2014 issued in U.S. Appl. No. 12/921,018.

Raspor et al., "Yeast Population Dynamics in Spontaneous and Inoculated Alcoholic Fermentations of Zametovka Must," Food Technol. Biotechnol., vol. 40, No. 2, pp. 95-102, Apr. 2002.

Salmon et al., "Improvement of nitrogen assimilation and fermentation kinetics under enological conditions by derepression of alternative nitrogen-assimilatory pathways in an industrial *Saccharomyces cerevisiae* strain", Applied and Environmental Microbiology, 1998, vol. 64, No. 10, pp. 3831-3837.

Wu et al., "Genetic diversity of the *Pichia membranifaciens* strains revealed from rRNA gene sequencing and electrophoretic karyotyping, and the proposal of *Candida califomica* comb. nov", FEMS Yeast Res., 2006, vol. 6, No. 2, pp. 305-311.

USPTO Non-final Office Action issued U.S. Appl. No. 12/921,018 (US 2011-0045140) dated Feb. 22, 2016; 11 pages.

* cited by examiner

Figure 1

AAACCAACAGGGATTGCCTCAGTAGCGGCGAGTGAAGCGGCAAGAGCTCAGATTTGAAAT
------------------------------------------------------TTTGAAAT
                                                       *******

CTCACCTAGTGTGCGAGTTGTAAATTGCAGGTTGGAGTCTCGGGTTAGACGTGTGTGCAA
CTCACCTAGTGTGCGAGTTGTAAATTGCAGGTTGGAGTCTCGGGTTAGACGTGTGTGCAA
************************************************************

GTCCCTTGGAACAGGGTGCCACTGAGGGTGAGAGCCCCGTANCGTGCATGTCGACACCTG
GTCCCTTGGAACAGGGTGCCACTGAGGGTGAGAGCCCCGTATCGTGCATGTCGACACCTG
****************************************  **************

TGAGGCCCTTCTGACGAGTCGAGTTGTTTGGGAATGCAGCTCTAAGTGGGTGGTAAATTC
TGAGGCCCTTCTGACGAGTCGAGTTGTTTGGGAATGCAGCTCTAAGTGGGTGGTAAATTC
************************************************************

CATCTAAGGCTAAATATTGGCGAGAGACCGATAGCGAACAAGTACTGTGAAGGAAAGATG
CATCTAAGGCTAAATATTGGCGAGAGACCGATAGCGAACAAGTACTGTGAAGGAAAGATG
************************************************************

AAAAGCACTTTGAAAAGAGAGTGAAACAGCACGTGAAATTGTTGAAAGGGAAGGGTATTG
AAAAGCACTTTGAAAAGAGAGTGAAACAGCACGTGAAATTGTTGAAAGGGAAGGGTATTG
************************************************************

GGCTCGACATGGGATTTACGCATCGTTGCCTCTCGTGGGCGGCGCTCTGGGTTTTCCTG
GGCTCGACATGGGATTTACGCATCGTTGCCTCTCGTGGGCGGCGCTCTGGGTTTTCCT-
*********************************************************

Figure 2

```
CACCTAAAATTGTAATACTACCAGTCACTAAGTTTTAACAAAACAAAACTTTCAACAACG
---------TTGTAATAATACCAGTCACTAAGTTTTAACAAAACAAAACTTTCAACAACG
         ******* ********************************************

GATCTCTTGGTTCTCGCATCGATGAAGAGCGCAGCGAAATGCGATACCTAGTGTGAATTG
GATCTCTTGGTTCTCGCATCGATGAAGAGCGCAGCGAAATGCGATACCTAGTGTGAATTG
************************************************************

CAGCCATCGTGAATCATCGAGTTCTTGAACGCACATTGCGCCCCATGGTATTCCATGGGG
CAGCCATCGTGAATCATCGAGTTCTTGAACGCACATTGCGCCCCATGGTATTCCATGGGG

************************************************************

CATGCCTGTCTGAGCGTCGTTTCCTTCTTGCGCAAGCAGAGTTGAGAACAGGCTATGCCT
CATGCCTGTCTGAGCGTCGTTTCCTTCTTGCGCAAGCAGAGTTGAGAACAGGCTATGCCT

************************************************************

TTTTCGAAATGGAACGTCGTGGACGAAGTGAACTAAATTTTTAGCACGCTTTGGCCGCCG
TTTTCGAAATGGAACGTCGTGGACGAAGTGAACTAAATTTTTAGCACGCTTTGGCCGCCG

************************************************************

AACTTTTAACTAAGCTCGACCTCAGATCAGGTAGGAATACCCGCTGAACTTAA
AAC---------------------------------------------------
***
```

Figure 3

```
AAACCAACAGGGATTGCCTCAGTAGCGGCGAGTGAAGCGGCAAGAGCTCAGATTTGAAAT
-----------------------------------------------------GATTTGAAAT
                                                     *********

CTCACCTAGTGTGCGAGTTGTAAATTGCAGGTTGGAGTCTCGGGTTAGACGTGTGTGCAA
CTCACCTAGTGTGCGAGTTGTAAATTGCAGGTTGGAGTCTCGGGTTAGACGTGTGTGCAA
************************************************************

GTCCCTTGGAACAGGGTGCCACTGAGGGTGAGAGCCCCGTANCGTGCATGTCGACACCTG
GTCCCTTGGAACAGGGTGCCACTGAGGGTGAGAGCCCCGTAGCGTGCATGTCGACACCTG
******************************************  ****************

TGAGGCCCTTCTGACGAGTCGAGTTGTTTGGGAATGCAGCTCTAAGTGGGTGGTAAATTC
TGAGGCCCTTCTGACGAGTCGAGTTGTTTGGGAATGCAGCTCTAAGTGGGTGGTAAATTC
************************************************************

CATCTAAGGCTAAATATTGGCGAGAGACCGATAGCGAACAAGTACTGTGAAGGAAAGATG
CATCTAAGGCTAAATATTGGCGAGAGACCGATAGCGAACAAGTACTGTGAAGGAAAGATG
************************************************************

AAAAGCACTTTGAAAAGAGAGTGAAACAGCACGTGAAATTGTTGAAAGGGAAGGGTATTG
AAAAGCACTTTGAAAAGAGAGTGAAACAGCACGTGAAATTGTTGAAAGGGAAGGGTATTG
************************************************************

GGCTCGACATGGGATTTACGCATCGTTGCCTCTCGTGGGCGGCGCTCTGGGTTTTTCCTG
GGCTCGACATGGGATTTACGCATCGTTGCCTCTCGTGGGCGGCGCTCTGGGTTTTTCCTG
************************************************************

GGCCAGCATCGGTTTTCGTTGCAGGATAAGGACAATTGGAATGTGGCTCCTCGGAGTGTT
GGCCAGCATCGGTTTTCGTTGCAGGATAAGANCAATTGGAATGTGGCTCCTCGGAGTGTT
*******************************  ***************************

ATAGCCTTTTGTAGATGCTGCGTATGGGGACCGAGGGCTGCGGCGGACTCGTTTCGTCTC
ATAGCCTTTTGTAGATGCTGCGTATGGGGACCGAGGGCTGCGGCGGACTCGTTTCGTCTC
************************************************************

GGATGCTGGCACAACGGCGCAATACCGC--------------------
GGATGCTGGCACAACGGCGCAATACCGCCCGTCTTGAAACACGGACCAA
****************************
```

Figure 4

```
-------------------------------------------AACCTGCGGAAGGATCATT
GTATANGATATAAATCACNGTAATGATCCTTCCGTAGGTGGAACCTGCGGAAGGATCATT
                                           ******************

ACTGTGATTTATATCTTATACACATGCGTGAGCGCACCAAACACCTAAAATTGTAATACT
ACTGTGATTTATATCTTATACACATGCGTGAGCGCACCAAACACCTAAAATTGTAATAMT
************************************************************ *

ACCAGTCACTAAGTTTTAACAAAACAAAACTTTCAACAACGGATCTCTTGGTTCTCGCAT
ACCAGTCACTAAGTTTTAACAAAACAAAACTTTCAACAACGGATCTCTTGGTTCTCGCAT
************************************************************

CGATGAAGAGCGCAGCGAAATGCGATACCTAGTGTGAATTGCAGCCATCGTGAATCATCG
CGATGAAGAGCGCAGCGAAATGCGATACCTAGTGTGAATTGCAGCCATCGTGAATCATCG
************************************************************

AGTTCTTGAACGCACATTGCGCCCCATGGTATTCCATGGGGCATGCCTGTCTGAGCGTCG
AGTTCTTGAACGCACATTGCGCCCCATGGTATTCCATGGGGCATGCCTGTCTGAGCGTCG
************************************************************

TTTCCTTCTTGCGCAAGCAGAGTTGAGAACAGGCTATGCCTTTTTCGAAATGGAACGTCG
TTTCCTTCTTGCGCAAGCAGAGTTGAGAACAGGCTATGCCTTTTTCGAAATGGAAMGTCG
******************************************************* ****

TGGACGAAG-TGAACTAAATTTTTAGCACGCTTTGGCCGCCGAACTTTTAACTAAGCTCG
TGGACGAAGGTGAACTAAATTTTTAGCACGCTTTGGCCGCCGAACTTT-AACTAAGCTCG
********* ************************************** **********

ACCTCAGATCAGGTAGGAATACCCGCTGAACTTAA
ACCTCAGATCAGGTAGG------------------
*****************
```

YEAST STRAINS AND METHODS OF USE THEREOF

CROSS REFERENCE TO RELATED APPLICATIONS

The present application is a divisional application of U.S. patent application Ser. No. 12/921,018, which was filed pursuant to 35 U.S.C. 371 as a U.S. National Phase application of International Patent Application No. PCT/NZ09/00029, which was filed Mar. 6, 2009, and claiming the benefit of priority to New Zealand Patent Application No. 5666518, which was filed on Mar. 7, 2008. The aforementioned applications are incorporated herein by reference in their entirety.

TECHNICAL FIELD

The present invention relates to yeast strains and, in particular, to yeast stains for use in fermentation processes. The invention also relates to methods of fermentation using the yeast strains of the invention either alone or in combination with other yeast strains. The invention further relates to methods for the selection of yeast strains suitable for fermentation cultures by screening for various metabolic products and the use of specific nutrient sources.

The invention has been developed primarily for use in the fermentation of grape juice and methods for producing wine, and will be described hereinafter with reference to this application. However, it will be appreciated that the invention is not limited to this particular field of use and that the invention may be useful in other fermentation processes.

BACKGROUND

Any discussion of the prior art throughout the specification should in no way be considered as an admission that such prior art is widely known or forms part of the common general knowledge in the field.

Fermentation is a process in which yeast metabolise simple sugars in fruit or vegetable matter primarily into ethyl alcohol and carbon dioxide. This process is involved in the production of a variety of comestible products such as bread, beer, wine, liquor, surface-ripened cheese and vinegar as well as in the production of biofuels, vitamins, and enzymes.

Wine is a product which is in part produced by alcoholic fermentation of grape juice by yeast. The yeast strains present in the fermentation process metabolise grape juice carbohydrates into ethanol and carbon dioxide. However, these components make a relatively minor contribution to the overall wine flavour. The aroma and flavor characteristics of wine result from a large number of compounds, including volatile acids and carbonyl compounds, 400 of which have been identified as being produced by yeast during the fermentation process (Nykanen, 1986).

Fermentation may proceed spontaneously, where the suite of microbes naturally present conduct the ferment; alternatively a winemaker may deliberately inoculate the grape juice with a large culture of a known commercially available wine yeast. The principle yeast used to inoculate grape juices are various strains of *Saccharomyces cerevisiae*.

The initial stages of spontaneous wine fermentation generally involve the growth of non-*Saccharomyces* yeasts, which exhibit low fermentative properties and thrive under a low alcohol milieu. These yeasts include *Hanseniaspora* (Kloeckera) and *Candida* (eg *Candida stellata, C. pulcherrima*) (Heard and Fleet, 1986) as well as other species. In the spontaneous case, fermentation involves the sequential interaction of a variety of yeast genera and species (Heard and -Fleet, 1988).

The sensitivity of non-*Saccharomyces* yeasts to environments of over 5% ethanol means that their growth is usually limited to the first 2 to 3 days of wine fermentation, following which the ethanol-tolerant *Saccharomyces* yeast become dominant. Importantly, the non-*Saccharomyces* strains can influence the fermentation significantly as they can reach populations of $10^6$-$10^7$ cells/ml (Lema et al., 1996). This influence includes the production of a wide range of volatile and non-volatile products such as organic acids, higher alcohols and esters that contribute substantially to the aroma and flavour characteristics of the wine (Rapp and Versini, 1991; Esteve-Zarzoso et al., 1998). The nature and concentrations of these "flavour compounds" are determined by the genera and species of the yeast present in the fermentation (Houtman et al., 1980; Lambrechts and Pretorius, 2000; Brandolini et al., 2002; Ramano et al., 2003). There is an increasingly large body of work examining the contribution of non-*Saccharomyces* species to wine flavour and aroma (Esteve-Zarzoso et al., 1998). Some of this work shows that mixed species ferments produce unexpectedly high levels of some flavour-active compounds including, for example, esters (Garde-Cerdan and Ancin-Azpilicueta, 2006; Rojas et al., 2003) and 2,3-butanediol (Clemente-Jiminez et al., 2004).

Volatile thiols are a family of flavour compounds found in wine (Gachons et al., 2000). They include, for example, 4-mercapto-4-methyl-pentan-2-one (4MMP), 4-mercapto-4-methyl-pentan-2-ol (4MMPOH), 3-mercaptohexan-1-ol (3MH) and 3-mercaptohexyl acetate (3MHA). Some of these thiols, eg. 3MH and 3MHA, have distinctive grapefruit- and passionfruit-like aromas and flavours (Tominaga et al., 1998a).

3MH and 3MHA are often found in Sauvignon Blanc (SB) wines at concentrations above the human sensory threshold. A cysteine-conjugated, non-volatile, flavourless precursor of 3MH, S-(3-hexan-1-ol)-cysteine, is found in SB grape juice, and during fermentation this precursor is potentially cleaved to liberate 3MH, which is subsequently converted to 3MHA (Gachons et al., 2000). The enzymes necessary for the processing of these precursors are thought to derive from yeasts, and conversion requires active yeast growth (Tominaga et al., 1998b). The enzymes involved are possibly some form β-lyase and acetyltransferase respectively. One publication has suggested that there are multiple yeast genes encoding β-lyase enzymes (Howell et al., 2005). However, scientists at two laboratories, including the present inventors, have been unable to repeat these results. To date, we consider that no robust data showing the precursors, enzymes or pathways responsible for the liberation of thiols by yeast have been published.

Chr Hansen (Denmark) produce four commercially available yeast starter cultures that include mixtures of different yeast species called Harmony, Symphony, Rhythm, and Melody. The yeast species included in these mixes are *S. cerevisiae, Torulaspora delbrueckii* and *Kluyveromyces thermotolerans*. The mixes have been reported to produce wines with an altered flavour profile but there has been no suggestion that the flavour profile is related to the presence, mix or concentration of thiols.

No studies have examined the effects of non-*Saccharomyces* species on the level of volatile thiols in wine or of the effects of mixtures of yeast species on thiol production or wine flavour. We are aware of only one study in which the effect of a *Saccharomyces* species on the level of volatile thiols in wine was measured. This related to the measurement of 4MMP produced by *Saccharomyces cerevisiae* in wine (Howell et al. 2004).

An understanding of the biological processes that control the presence and amount of compounds in a fermentation process is highly desirable. In particular, being able to regulate the amount and type of thiols in wine would be very beneficial to winemakers.

Regulation of the amount of thiols, and in particular 3MH and 3MHA, in wine would allow for the development of new technologies permitting wine makers to more precisely alter the amounts of these distinctive flavour compounds in their product. Such a technology would, therefore, be of significant commercial value.

It is an object of the present invention to overcome or ameliorate at least one of the disadvantages of the prior art, or to provide a useful alternative.

SUMMARY OF INVENTION

It has unexpectedly been found that certain yeast strains have advantageous properties useful in the fermentation process. In particular, the yeast strains can be combined with other yeast in a fermentation process to produce a synergistic effect—namely, the production of increased thiols in the fermentation product. More specifically, the yeasts can be used to produce increased levels of 3MH and 3MHA in wine. In addition, certain new strains that produce increased thiols in the fermentation process are able to access a source of nitrogen and carbon not usually accessible to yeast of their species in ferments, namely proline.

The inventors surprisingly found that, for example, the yeast strains named PK-KR1 and PK-KR2 (two novel strains of *Pichia kluyveri*), act synergistically with commercially available yeast strains to produce elevated levels of volatile thiols in wine fermentation cultures. Within a ferment the relatively limiting amounts of nitrogen available to yeasts may critically affect the process of fermentation and the side products produced by yeasts. It has further been surprisingly found that particular yeast strains are able to utilise nutrient sources unavailable to commercial *S. cerevisiae* preparations in a fermentation culture. For example, the PK-KR1 strain has a greater propensity to utilise L-proline as a source of both nitrogen and carbon than *S. cerevisiae*. Proline is one of the most abundant amino acids in grape juice but is not utilised by *S. cerevisiae*. Thus, the use of PK-KR1 not only unexpectedly alters the final flavour and aroma of wine but during the ferment process competition for relatively limiting nutrients (nitrogen) between PK-KR1 and commercial *S. cerevisiae* preparations is alleviated.

As such, the present invention relates to yeast strains, yeast fermentation starter cultures and methods of fermentation that allow for increased production of thiols and novel nutrient use. Accordingly, in a first aspect, the present invention provides an isolated yeast strain as deposited at the National Measurement Institute under accession number V06/022711 or V06/022712 or a functional equivalent thereof as herein defined. These isolates were deposited under the names JTI.28 and JT3.71, respectively for PK-KR1 and PK-KR2.

According to a second aspect, the present invention provides an isolated yeast strain comprising a nuclear ribosomal internal transcribed spacer (ITS) 1-5.8S-ITS2 nucleotide sequence according to anyone of SEQ ID NOS: 5 or 6.

According to a third aspect, the present invention provides an isolated yeast strain comprising a divergent domain 1 and 2 (D1/2) 26S rDNA nucleotide sequence according to SEQ ID NOS: 7 or 8.

According to a fourth aspect, the present invention provides a method of fermentation comprising use of a yeast strain according to the first, second or third aspect.

The yeast strains of the present invention may be used with one or more other yeast strains in a fermentation process to produce a synergistic increase in thiol production.

According to a fifth aspect, the present invention provides a method of fermentation comprising use of a first yeast strain according to the first, second or third aspect and a second yeast strain wherein said method includes the step of adding said first yeast strain and said second yeast strain to a fermentation culture thereby resulting in a synergistic increase in thiol production in a fermentation product produced by the method.

Preferably, the fermentation product is an alcoholic beverage. More preferably, the alcoholic beverage is wine. Most preferably, the wine is white wine. In a particularly preferred embodiment, the white wine is produced from grapes of sauvignon blanc variety.

Preferably, one of the yeast strains is a non-*Saccharomyces* strain. More preferably, the non-*Saccharomyces* strain belongs to the *Pichia* genera, even more preferably the non-*Saccharomyces* strain is a member of the *Pichia kluyveri* species. In a particularly preferred embodiment the non-*Saccharomyces* yeast strain is the strain deposited at the National Measurement Institute under the accession number V06/022711 or V06/022712 or a functional equivalent thereof.

Preferably, one of the yeast strains is a *Saccharomyces* strain. More preferably, the *Saccharomyces* strain is a commonly available strain selected from VL3, VIN 7, X5 or 'Merit' as described herein.

It will be clear to the skilled addressee that the thiol may be any thiol or any combination of thiols. The thiols are preferably volatile. In one preferred embodiment, the thiol is 3-mercaptohexyl acetate (3MHA) and in another preferred embodiment, the thiol is 3-mercaptohexan-1-ol (3MH).

It will also be clear to the skilled addressee that the first and second yeast strains may be added to a ferment simultaneously or sequentially.

According to a sixth aspect, the present invention provides a fermentation yeast starter culture comprising at least two yeast strains that produce a synergistic increase in thiol in a fermentation product.

Preferably, one yeast strain is a non-*Saccharomyces* strain.

In one embodiment, the non-*Saccharomyces* strain comprises greater than 10% of the total yeast concentration present in the starter culture. Preferably, the total yeast concentration present in the starter culture is $2.5 \times 10^6$ cells ml$^{-1}$. In another embodiment, the non-*Saccharomyces* strain comprises greater than 20% of the total yeast present in the starter culture. In another embodiment, the non-*Saccharomyces* strain comprises greater than 30% of the total yeast present in the starter culture. In another embodiment, the non-*Saccharomyces* strain comprises greater than 40% of the total yeast present in the starter culture. In another embodiment, the non-*Saccharomyces* strain comprises greater than 50% of the total yeast present in the starter culture. In another embodiment, the non-*Saccharomyces* strain comprises greater than 60% of the total yeast present in the starter culture. In another embodiment, the non-*Saccharomyces* strain comprises greater than 70% of the total yeast present in the starter culture. In another embodiment, the non-*Saccharomyces* strain comprises greater than 80% of the total yeast present in the starter culture. In a further embodiment, the non-*Saccharomyces* strain comprises about 90% of the total yeast present in the starter culture. In another embodiment, the non-*Sac-*

*charomyces* strain comprises greater than 90% of the total yeast present in the starter culture. In another embodiment, the total yeast concentration present in the starter culture exceeds $2.5 \times 10^6$ cells ml$^{-1}$. Preferably, the non-*Saccharomyces* strain is the yeast deposited at the National Measurement Institute under the accession number V06/022711 or V06/022712. In one embodiment, the thiol synergistically increased in the fermentation product is 3MHA and in an alternative embodiment the thiol synergistically increased in the fermentation product is 3MH. It will be clear to the skilled addressee, of course, that there may be a synergistic increase in more than one thiol.

According to a seventh aspect, the present invention provides a method of producing a fermentation product comprising use of the starter culture according to the invention wherein said method comprises the step of adding said starter culture to a fermentation culture. Preferably, the fermentation product is an alcoholic beverage and most preferably the alcoholic beverage is wine.

According to an eighth aspect, the present invention provides a beverage prepared according to the method of the invention. Preferably, the beverage is alcoholic and more preferably it is wine.

Most preferably, the wine is white wine. In a particularly preferred embodiment, the white wine is produced from grapes of the sauvignon blanc variety.

It has also been unexpectedly found that the novel yeast isolates, for example PK-KR1, are capable of utilising novel sources of nitrogen and carbon in fermentation cultures.

According to a ninth aspect, the present invention provides a method of fermentation comprising use of a yeast strain wherein said method comprises the step of adding said yeast strain to a fermentation culture and said yeast strain is capable of deriving nitrogen and/or carbon from an amino acid under fermenting conditions. Preferably, the amino acid is proline.

According to a tenth aspect, the present invention provides a method of fermentation wherein said method comprises the step of adding proline to a fermentation culture wherein said proline is a source of nitrogen and/or carbon for a yeast strain in said fermentation culture.

According to an eleventh aspect, the present invention provides a method of fermentation comprising use of two yeast strains wherein said method comprises the step of adding said strains to a fermentation culture and each of said strains are capable of deriving nitrogen and/or carbon from different sources.

According to a twelfth aspect, the present invention provides a method of selecting a yeast for a fermentation culture said method comprising the step of adding a yeast strain to a fermentation culture having proline as its substantially only source of Nitrogen and isolating a yeast strain from said culture which exhibits a capacity of deriving nitrogen from proline.

According to a thirteenth aspect, the present invention provides a method of fermentation comprising the use of a yeast strain said method comprising the step of adding a yeast strain to a fermentation culture and wherein said yeast strain does not use glucose or fructose as its sole or substantially sole carbon source.

According to a fourteenth aspect, the present invention provides a method of enhancing flavour in a product of fermentation, said method comprising use of a yeast strain according to any of the claims or a yeast starter culture according to any one of the claims in a fermentation culture said method comprising the step of adding said yeast strain or said starter culture to a fermentation culture.

In the context of the present invention, the term "functional equivalent thereof", insofar as it relates to the functional equivalent of a yeast strain described or defined in the present application, refers to, in one embodiment, the capacity of the yeast strain to interact with at least one other yeast strain to produce a synergistic increase in the amount of thiol in a fermentation product wherein the "at least one other yeast strain" is not PK-KR1 or PK-KR2. In an alternative embodiment, the term "functional equivalent thereof" refers to a yeast strain with a capacity to access a source of nitrogen and/or carbon in ferment cultures not usually accessible to yeasts of their species.

In the context of the present invention, a "synergistic increase" insofar as it relates to the amount of thiol in a fermentation product means an increase in the amount of thiol in a fermentation product produced by two yeast strains, in excess of the sum of thiol produced in a fermentation product by either one of the yeast strains alone.

In the context of the present invention, the term "fermentation product" includes any product of a fermentation process including solid, liquid or gaseous products.

In the context of the present invention the term "strain" insofar as it relates to yeast refers to a potential genetic variant or sub-type within a species; for example, an isolate of a species from a particular place in time, or an isolate which may be demonstrated to differ from other members of the same species at the nucleotide level.

In the context of the present invention the term "fermentation" refers to a process in which yeast metabolise simple sugars in fruit or vegetable matter primarily into ethyl alcohol and carbon dioxide.

In the context of the present invention, the terms "comprise", "comprising" and the like are to be construed in their inclusive sense ie. in the sense of "including but not limited to" rather than in their exhaustive sense.

BRIEF DESCRIPTION OF THE FIGURES

FIG. 1: Nucleotide sequence homology alignments of PK-KR1 D1/D2 area of the 26S ribosomal gene with the type strain of *Pichia kluyveri*.

Top sequence=*P. kluyveri* type strain (CBS188), accession U75727

Bottom sequence=PK-KR1

FIG. 2: Nucleotide sequence homology alignments of PK-KR1 ITS area with the same area from the type strain of *Pichia kluyveri*.

Top sequence=*P. kluyveri* type strain (CBSI88), accession DQ104711

Bottom sequence=PK-KR1

FIG. 3: Nucleotide sequence homology alignments of PK-KR2 D1/2 area of the 26S ribosomal gene with the same area of the type strain of *Pichia kluyveri*.

Top sequence=*P. kluyveri* type strain (CBS 188), accession U75727

Bottom sequence=PK-KR2

FIG. 4: Nucleotide sequence homology alignments of PK-KR2 ITS area with the same area from the type strain of *Pichia kluyveri*.

Top sequence=*P. kluyveri* type strain (CBS 188), accession DQ104711

Bottom sequence=PK-KR2

Figure 5:
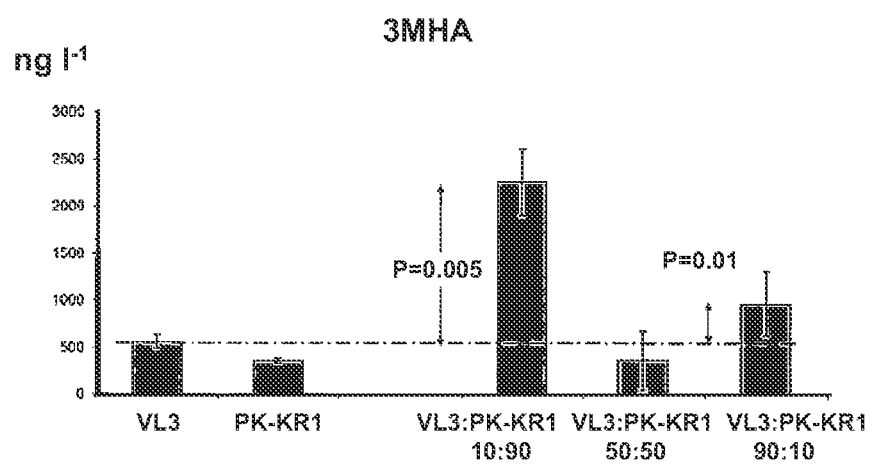

FIG. 5: A bar graph showing the concentration of 3MHA produced in single and mixed ferments containing yeast strains VL3 and PK-KR1 at ratios of: 10:90, 50:50 and 90:10.

Figure 6:
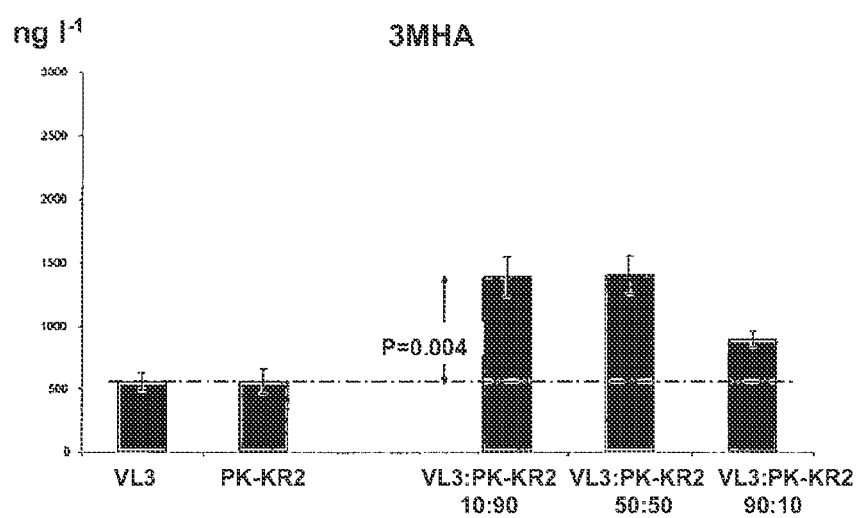

FIG. 6: A bar graph showing the concentration of 3MHA produced in single and mixed ferments containing yeast strains VL3 and PK-KR2 at ratios of: 10:90, 50:50 and 90:10.

Figure 7:
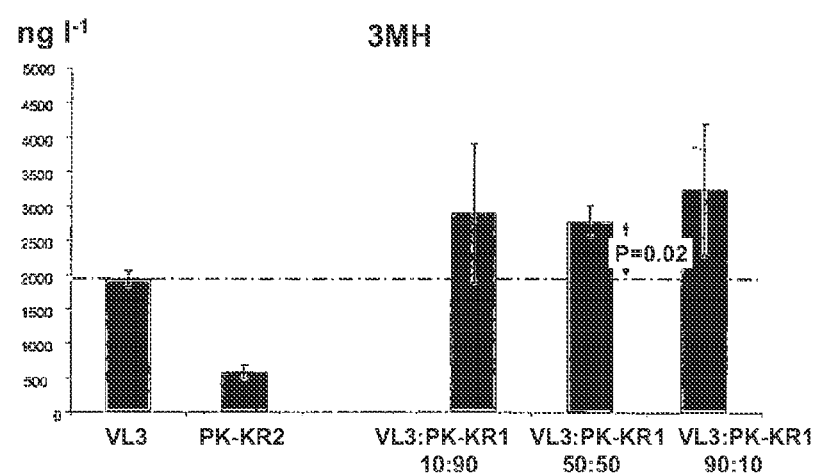

FIG. 7: A bar graph showing the concentration of 3MH produced in single and mixed ferments containing yeast strains VL3 and PK-KR1 at ratios of: 10:90, 50:50 and 90:10.

Figure 8:
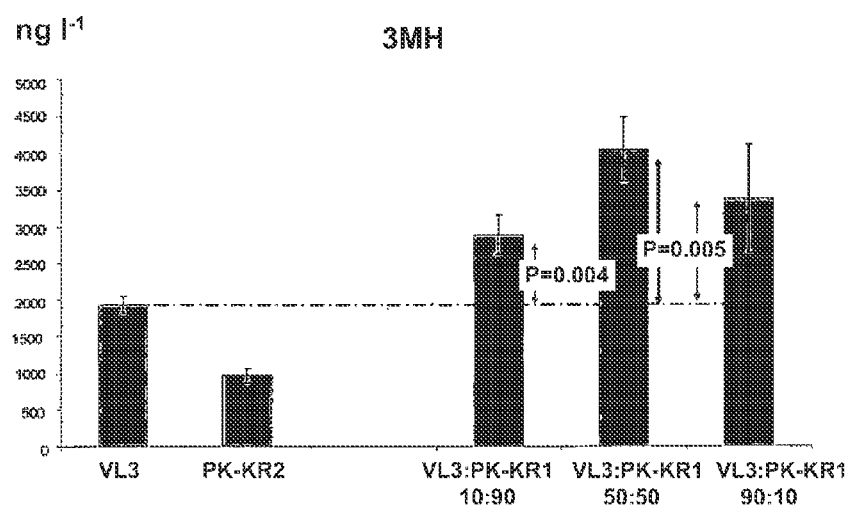

FIG. 8: A bar graph showing the concentration of 3MH produced in single and mixed ferments containing yeast strains VL3 and PK-KR2 at ratios of: 10:90, 50:50 and 90:10.

Figure 9:
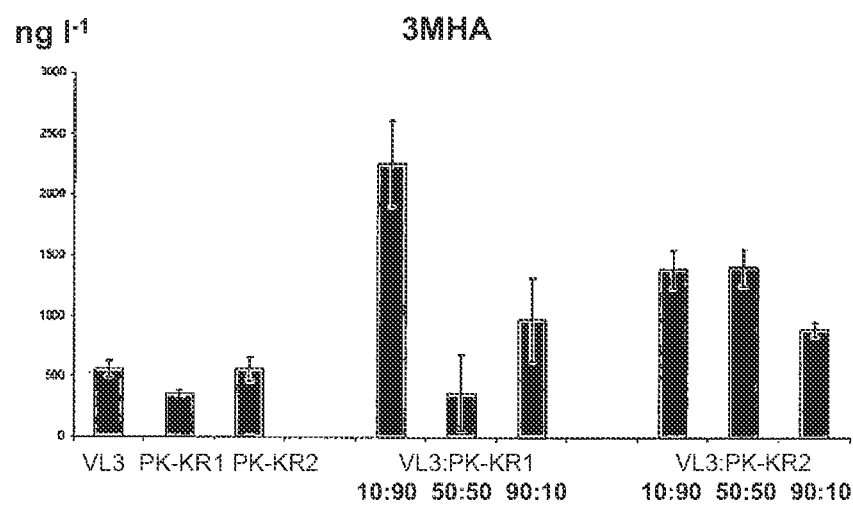

FIG. 9: A bar graph combining data presented in FIGS. 3 and 4 showing the concentration of 3MHA produced in single and mixed ferments containing yeast strains VL3, PK-KR1, PK-KR2, and combinations as follows: VL3: PK-KR1; VL3: PK-KR2; at ratios of 10:90, 50:50 and 90:10.

Figure 10:
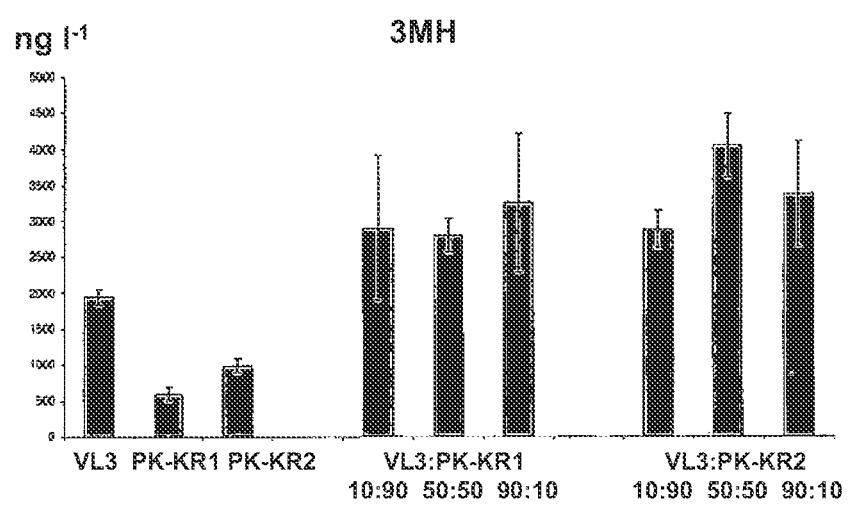

FIG. 10: A bar graph combining data presented in FIGS. 5 and 6 showing the concentration of 3MH produced in single and mixed ferments containing yeast strains VL3, PK-KR1, PK-KR2, and combinations as follows: VL3: PK-KR1; VL3: PK-:KR2; at ratios of 10:90, 50:50 and 90:10.

Figure 11:
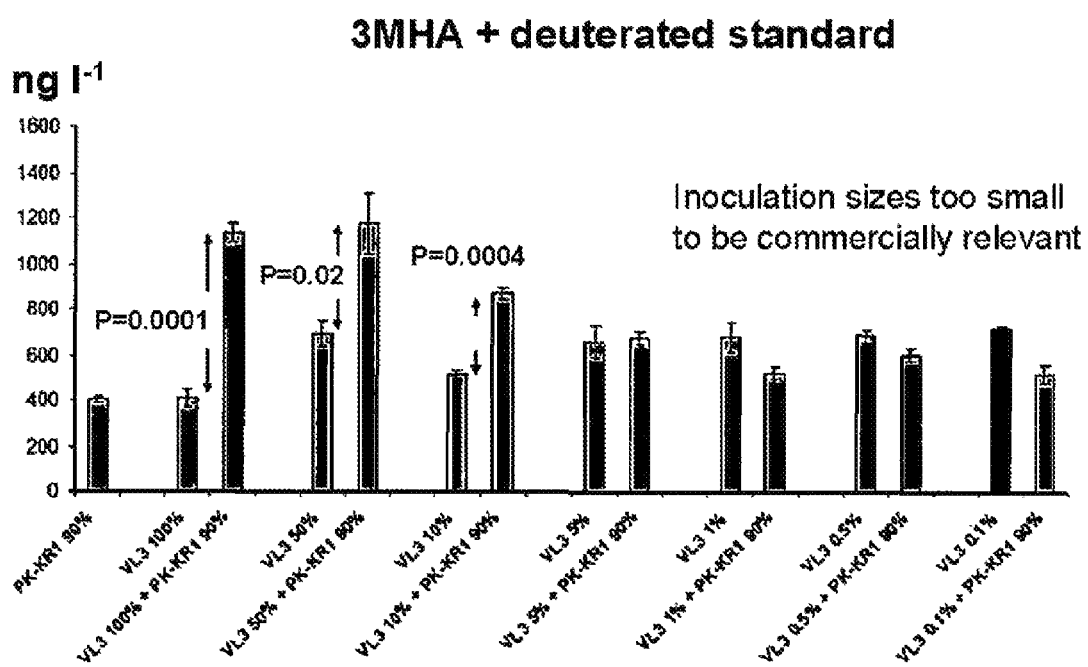

FIG. 11: A bar graph showing the concentration of 3MHA (using a deuterated standard) in single and mixed ferments of PK-KR1 and VL3.

Figure 12:
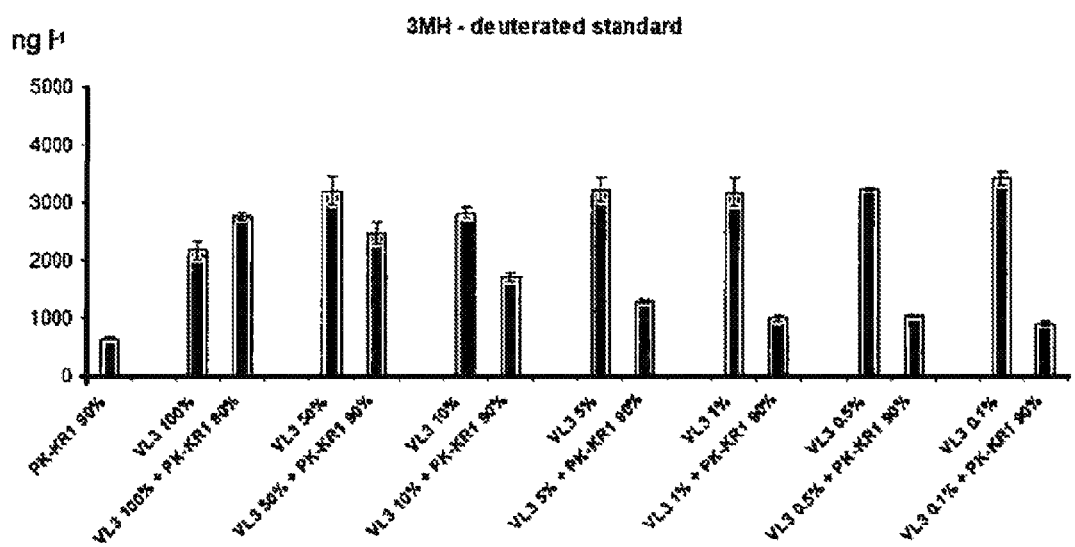

FIG. 12: A bar graph showing the concentration of 3MH (using a deuterated standard) in single and mixed ferments of PK-KR1 and VL3.

Figure 13A:
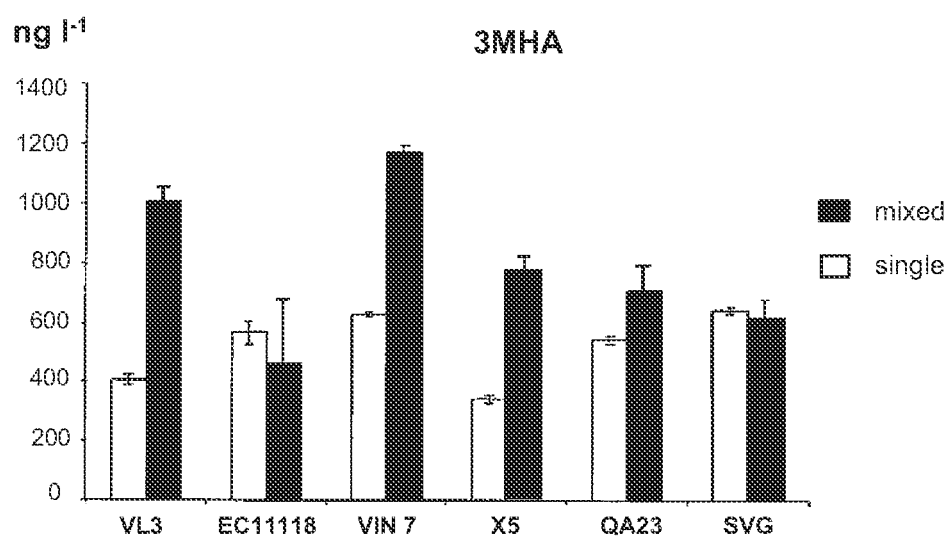

FIG. 13a: A bar graph showing the concentration of 3MHA produced in single and mixed ferments (fermentation temperature 14° C.) with PK-KR1 and a variety of commercial wine strains VL3, EC1118, VIN7, X5, QA23 and SVG.

Amounts of 3MHA (a) and 3MH (b) (mean±s.e.m; n=3) produced by a set of commercial wine yeasts in single and co-ferment at 14° C. with PK-KR1. The co-ferments were all initiated at 10:90 *S. cerevisiae*:PK-KR1. The levels of 3MHA in PK-KR1 co-ferments with VL3, VIN7 and X5 are all significantly higher compared to the respective VL3, VIN7 and X5 single ferments (p<0.01).

Figure 13B:
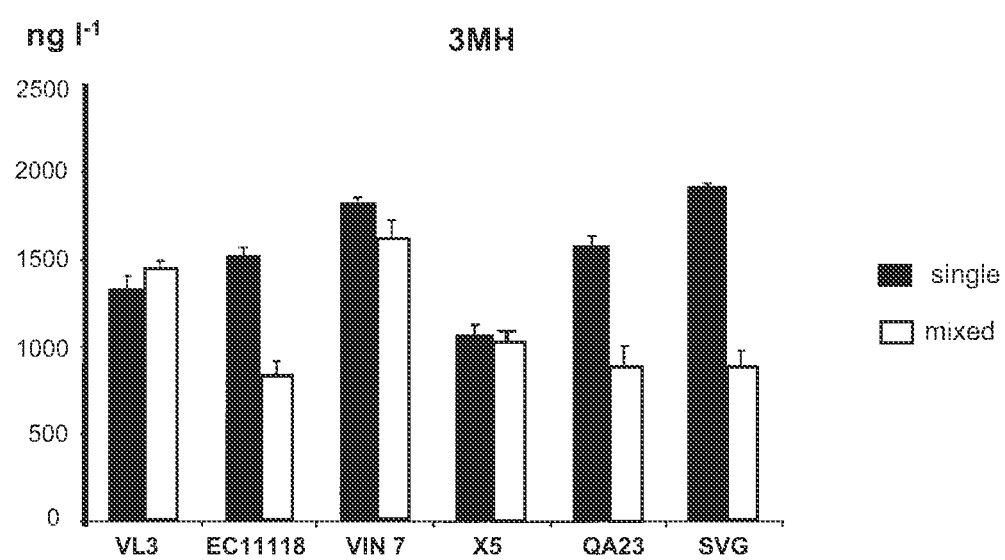

FIG. 13b: A bar graph showing the concentration of 3MH produced in single and mixed ferments (fermentation temperature 14° C.) with PK-KR1 and a variety of commercial wine strains VL3, EC1118, VIN7, X5, QA23 and SVG.

Figure 14:
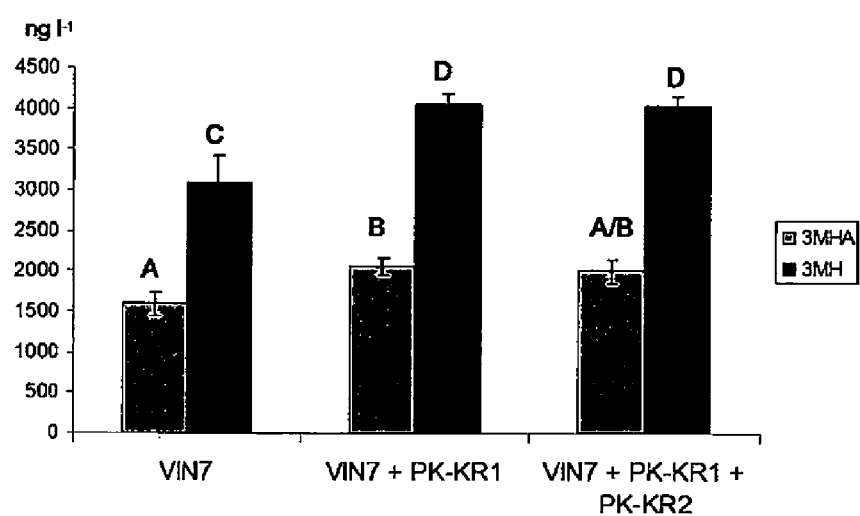

FIG. 14: A bar graph showing the concentration of 3MHA and 3MH produced in 5 litre mixed ferments (fermentation temperature 14° C.) with PK-KR1, PK-KR2 and VIN7. 3MHA and 3MH levels are in ng $l^{-1}$; levels not connected by the same letter are significantly different by at-test (P>0.05).

Five litre mixed ferment experiment 3MHA and 3MH levels are in ng $l^{-1}$; levels not connected by the same letter are significantly different by at-test (P>0.05).

Figure 15:
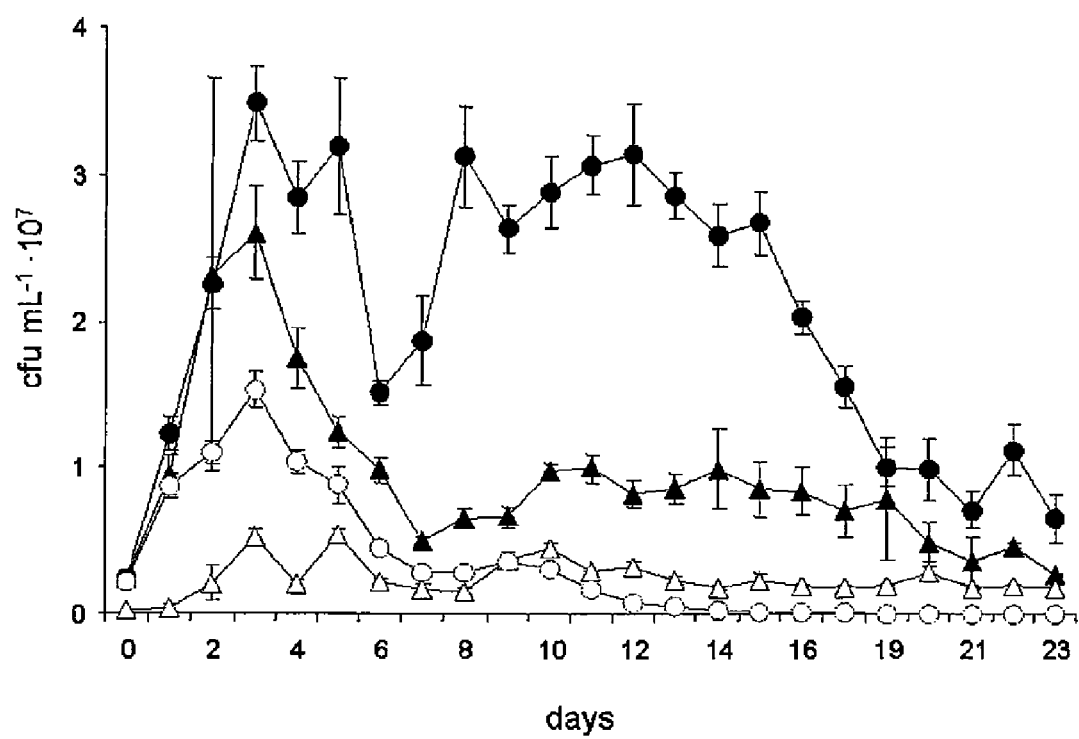

FIG. 15: Cell numbers estimated by colony forming units of VL3 and PK-KR1 in single ferments and co-ferments in Sauvignon blanc juice.

Cell numbers estimated by colony forming units of VL3 and PK-KR1 in single ferments (solid triangle and circles respectively) and co-ferments (open triangle and circle respectively) at 14° C. The co-ferment was inoculated with a 10:90 ratio of VL3/PK-KR1. mean±s.e.m; n=6.

Figure 16:
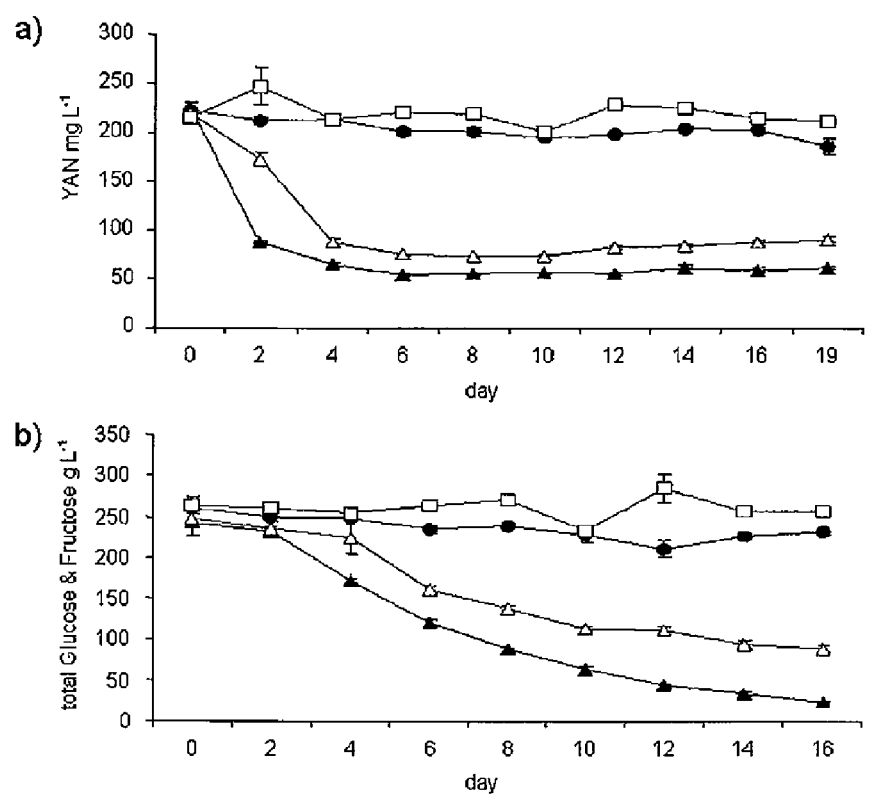

FIG. 16: Nutrient use during single and mixed ferments, (a) YAN, and (b) glucose and fructose use by PK-KR1 and VL3 during single and mixed ferments.

a) Change in the amount of yeast available nitrogen (YAN) during VL3 single ferments (solid triangle) and co-ferments (open triangle) respectively and PK-KR1 single ferment (solid circle) at 14° C. The co-ferment was initiated at 10:90 VL3 to PK-KR1 ratio. Control, un-inoculated sterile grape juice (open squares), mean±s.e.m; n=3.

b) Change in the amount of total glucose and fructose during VL3 single (solid triangle) and co-ferments (open triangle) respectively and PK-KR1 single ferment (solid circle) at 14° C. The co-ferment was initiated at 10:90 VL3 to PK-KR1 ratio. Control, un-inoculated sterile grape juice (open squares), mean±s.e.m; n=3.

Figure 17:
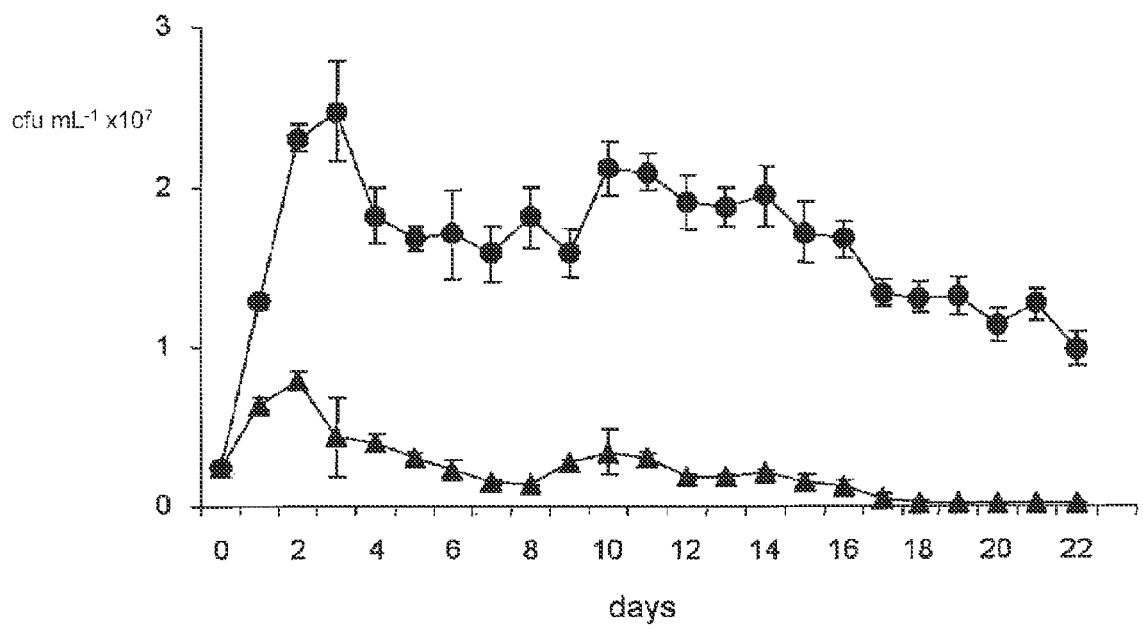

FIG. 17: The growth of PK-KR1 and VL3 in media containing proline as the only nitrogen source under ferment conditions.

The growth of VL3 (triangles) and PK-KR1 (circles) during ferment conditions at 14° C. in a defined Yeast Nitrogen Base medium where Proline was the only nitrogen source. mean±s.e.m; n=6.

Figure 18:
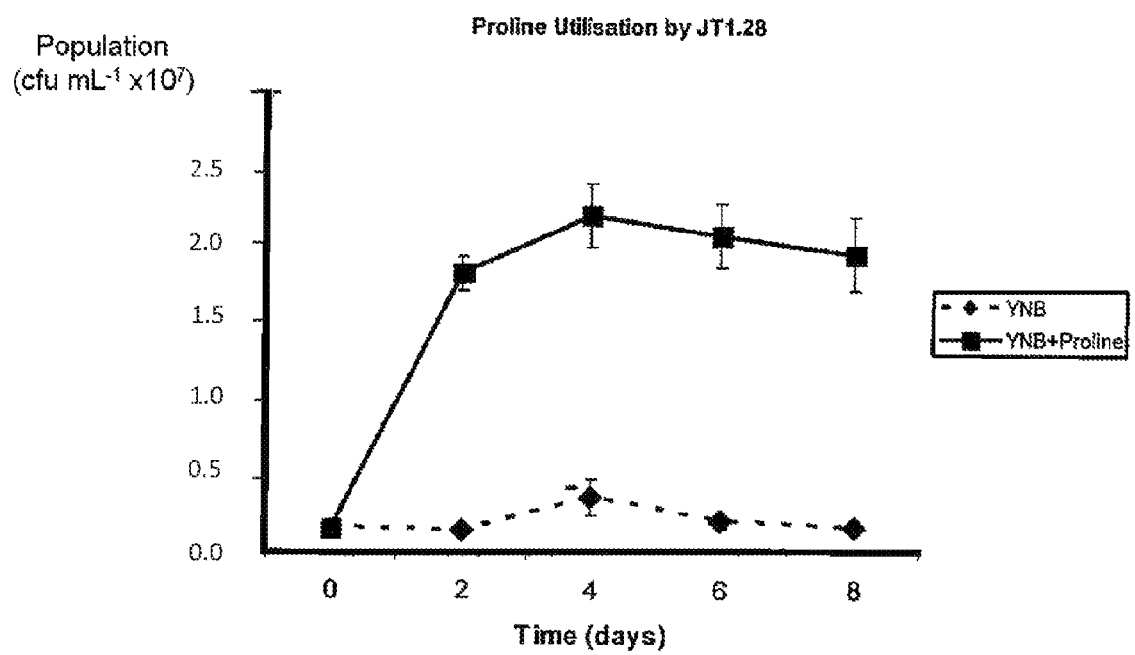

FIG. 18: The growth of PK-KR1 under ferment conditions after being starved for carbon and nitrogen in media containing proline as the only nitrogen source.

Growth of PK-KR1 (after being starved for carbon and nitrogen) in a YNB alone (therefore no C or N source supplied), and an identical media except where proline has been added.

DESCRIPTION OF THE INVENTION

The present invention relates to yeast strains and, in particular, to yeast stains for use in fermentation processes.

The invention also relates to yeast strains PK-KR1 and PK-KR2 deposited under the names JT1.28 and JT 3.71 at the National Measurement Institute, 51-65 Clarke Street, South Melbourne Victoria 3205, under accession numbers V06/022711 and V06/022712 respectively.

SB wines produced for example in the Marlborough region of the South Island in New Zealand have very distinctive flavour profiles. This distinctive style places these wines in a strong position in the international wine market. Accordingly, yeasts involved in enhancing the aroma and/or flavour of these wines are commercially valuable.

The invention also relates to methods of fermentation using the yeast strains either alone or in combination with others.

The invention further relates to methods for screening and isolating yeast strains suitable for fermentation cultures and in particular yeasts that enhance one or more characteristics of wine such as the flavour and/or aroma.

Preferably, the screening method comprises inoculating a ferment culture or medium or a number of ferment cultures or media with a yeast strain or number of yeast strains. Preferably the culture or medium contains a substantially single pre-selected carbon and/or nitrogen source. Preferably the source of carbon and/or nitrogen is proline. The method further comprises incubating the inoculated ferment or culture at a temperature suitable for growth of the yeast and monitoring yeast growth over a period of time. The method further comprises identification and isolation of a yeast strain or yeast strains that are capable of using the substantially single pre-selected carbon and/or nitrogen source as a nutrient source.

Nitrogen is usually a limiting essential resource for yeasts in grape juice—the relatively low levels of nitrogen can temper yeast growth and fermentation and possibly lead to fermentation problems (stuck ferments for example) (Ribereau-Gayon et al. 2006). Of the sources of nitrogen that are present in grape juice, yeast utilise ammonia first, and then amino acids. Proline is usually one of the most abundant amino acids in grape juice (Ough and Stashak 1974; Spayd and Andersen-Bagge 1996). However, *S. cerevisiae* is unable to utilize proline under anaerobic conditions (the PutI enzyme in the *S. cerevisiae* degradation pathway requires $O_2$; Ingledew et al. 1987). In this respect, an important source of nitrogen is unavailable to *S. cerevisiae* during fermentation—if yeast were able to utilise proline as a nitrogen and or carbon source by some means, problems occurring during fermentation may be alleviated, for example wine makers need not artificially add nitrogen sources. Further, from a non-*Saccharomyces* co-fermentation perspective, a co-fermenting partner that does not directly compete for limited nitrogen resources (by being able to access proline for example) would be ideal in commercial applications, since this not only lessens competition with *S. cerevisiae*, but also unlocks the nitrogen hidden in proline for subsequent use by *S. cerevisiae*.

Accordingly, the invention further relates to yeast strains capable of utilising novel sources of nitrogen and/or carbon in fermentation cultures.

The invention is further described by the following non-limiting examples.

EXAMPLES

Example 1

Yeast Isolation

Two yeast strains, designated PK-KR1 and PK-KR2, were isolated from the natural fermentation of the 2005 Chardonnay grape juice obtained from Mate's vineyard in Kumeu River Wines, West Auckland as described below. FIGS. 1 to 16 show experimental data relating to experiments carried out using these strains and reported in more detail below.

Samples of juice were taken at various stages during the fermentation process and inoculated into acidified malt media to select for yeast and against bacteria (Johnson et al., 2004). DNA was extracted using protocols well known in the art from isolated yeast-like colonies using Chelex-100 chelating resin (Walsh et al 1991). The nuclear ribosomal internal transcribed spacer (ITS) I, S.8S, and ITS2 and 26S divergent domains 1 and 2 (D1/D2) of each strain were amplified using primers specific to fungi (White et al., 1990, Kurtzman and Robnett 1998), by the polymerase chain reaction by methods well known in the art. The skilled addressee would understand that these regions of the yeast genome are traditionally analysed to identify organisms to the species level (Leaw et al. 2006 and White et al., 1990, Kurtzman and Robnett 1998). Specifically, the nuclear ribosomal internal transcribed spacer (ITS) 1, 5.8S, and ITS2 sequences were amplified using primers designated SEQ ID NO 1 and SEQ ID NO 2 and the 26S divergent domains 1 and 2 (D1/D2) sequences were amplified using primers designated SEQ ID NO 3 and SEQ ID NO 4. Both strands of the resulting DNA products were sequenced using methods well known in the art. The ITS1-5.8S-ITS2 DNA sequence of yeast PK-KR1 and PK-KR2 are designated SEQ ID NO: 5 and 6 respectively. The 26S D1/2 DNA sequence of yeast PK-KR1 and PK-KR2 are designated SEQ ID NO:7 and 8 respectively.

The ITS1-5.8S-ITS2 DNA and 26S domain 1 and 2 sequences from these strains were analysed using the standard BLAST search tool available at the NCBI website, in accordance with Kurtzman & Fell, (2006). The relevant sequence homology alignments are shown in see FIGS. 1 to 4. The analysis indicates that the isolated yeasts are novel strains of *Pichia kluyveri* as detailed below.

PK-KR1

Alignment of ITS region of PK-KR1 indicated a: 99% identity to DQ674358 (*Pichia fermentans*) and DQ104711 (*Pichia kluyveri*)

Alignment of 26S region of PK-KR1: indicated a 100% identity to EF564382.1 (*Pichia kluyveri*)

The PK-KR1 sequences indicated above were also aligned to corresponding sequences U75727 and DQ104711 of *Pichia kluyveri*. These alignments are shown in FIGS. 1 and 2 respectively.

PK-KR2

Alignment of ITS region of PK-KR2 indicated a 98% identity to AY027508.1/DQ104711.1 (*Pichia fermentans/Pichia kluyveri*)

Alignment of 26S region of PK-KR2 indicated a 99% identity to AJ746339.1 (*Pichia kluyveri*)

The PK-KR2 sequences indicated above were also aligned to corresponding sequences U75727 and DQ104711 of *Pichia kluyveri*. These alignments are shown in FIGS. 3 and 4

Conclusion—PK-KR1 and PK-KR2 are two different and novel strains of *Pichia kluyveri*

| Our identifier | Best species match |
|---|---|
| PK-KR1 | *Pichia kluyveri* |
| PK-KR2 | *Pichia kluyveri* |

Example 2

Micro-Fermentation with Isolated Yeast in Single and Mixed Cultures

Fermentation was carried out using the yeast isolates prepared in Example 1 and the yeast strain Zymaflore VL3 (Laffort). This is a commercially available strain of *Saccharomyces cerevisiae*, isolated in Bordeaux and sold specifically for wine fermentation.

Ferments were conducted using 200 mL of sterile 2005 Sauvignon Blanc grape juice from Rapaura in Marlborough. The grape juice was first sterilised using DMDC (dimethyl dicarbonate, $C_4H_6O_5$, MW: 134.09 gmol$^{-1}$, CAS: 4525-33-1).

Ferments were conducted using single strains, and with various pair-wise proportions of strains as indicated in Table 1 below. Each yeast species was cultured for 48 hours at 28° C. in a standard yeast laboratory medium before inoculating the juice. Consistent with the wine industry protocols, the juice was inoculated to an initial concentration of $2.5 \times 10^6$ yeast cells mL$^{-1}$. Inoculation described is referred to by percentages, with 100% corresponding to $2.5 \times 10^6$ yeast cells mL$^{-1}$.

Two independent sets of ferments were conducted. The first sets of ferments were designed to investigate the effect of mixed species ferments on thiol concentrations. The proportions of yeast used in these ferments are summarised in Table 1.

TABLE 1

Mixed ferment yeast inoculation proportions as a percentage of 2.sx106 cells ml$^{-1}$

| Commercial Yeast strain | Inoculation load | Yeast Isolate | Inoculation load |
|---|---|---|---|
| VL3 | 10% | PK-KR1 | 90% |
| VL3 | 50% | PK-KR1 | 50% |
| VL3 | 90% | PK-KR1 | 10% |
| VL3 | 10% | PK-KR2 | 90% |
| VL3 | 50% | PK-KR2 | 50% |
| VL3 | 90% | PK-KR2 | 10% |

A second set of ferments was conducted to investigate the effect of inoculum size on final thiol concentration, and to corroborate the results of the initial ferments with respect to the VL3 and PK-KR1 mixed ferments. The inoculum size and proportion of yeast inoculums are shown in Tables 2 and 3.

TABLE 2

Inoculum size as a percentage of 2.5 × 10⁶ cells ml⁻¹

| Yeast Strain | Inoculum size |
|---|---|
| VL3 | 100% |
| VL3 | 50% |
| VL3 | 10% |
| VL3 | 5% |
| VL3 | 1% |
| VL3 | 0.5% |
| VL3 | 0.1% |
| PK-KR1 | 90% |

TABLE 3

Mixed ferment yeast inoculation proportions as a percentage of 2.5 × 10⁶ cells ml⁻¹

| Commercial Yeast strain | Inoculation load | Yeast Isolate | Inoculation load |
|---|---|---|---|
| VL3 | 100% | PK-KR1 | 90% |
| VL3 | 50% | PK-KR1 | 90% |
| VL3 | 10% | PK-KR1 | 90% |
| VL3 | 5% | PK-KR1 | 90% |
| VL3 | 1% | PK-KR1 | 90% |
| VL3 | 0.5% | PK-KR1 | 90% |
| VL3 | 0.1% | PK-KR1 | 90% |

Ferments were carried out at 25° C. in 250-mL Erlenmeyer flasks with an air lock. Fermentation progress was monitored by weight loss since this approximately corresponds to the degree to which the sugars in the juice have been metabolised to ethanol and $CO_2$. After a seven-day ferment the contents of the flasks were centrifuged at 6000×g for 10 min to pellet any solids. The supernatant was then transferred to 70-mL sample containers and stored at −20° C. All fermentations were performed in triplicate.

Thiol Extraction and Quantification

The thiol concentration in the ferment liquid (wine) was analysed based on the method of Tominaga et al. (Tominaga et al., 1998c), requiring thiol separation from the wine by chromatography followed by analysis using gas chromatography mass spectrometry (GC-MS) according to standard procedures. The quantification method relies on comparison to a known amount of an internal standard added to the wine before processing.

Thiol Separation from the Wine

Five mL of 1 mM Na-4-(hydroxymercuri)benzoate (pHMB), and 0.5 mL of 2 mM 0.1 M Na-acetate, pH6, 0.02 mM Butylated Hydroxyanisole (BHA) were added to each 50-mL wine sample, and mixed before adding a mixture of the deuterated forms of 3MH and 3MHA. The pH was then adjusted to 7.

The samples were then passed through a Dowex resin column and any thiols present bound to the matrix in the column. The column was then washed with 50 mL of BHA. The bound thiols were then eluted with 50 mL cysteine elution buffer (0.1M Na-acetate, 0.02 mM BHA, 400 mg Cysteine-HCl, adjusted to pH6).

The thiols in the eluted solution were extracted with dichloromethane. The lower organic phase containing the thiols was recovered and then dried with anhydrous $Na_2SO_4$, before being filtered and concentrated under a $N_2$ gas flow to a final volume of approximately 25 µL.

GC-MS Analysis

Three microlitres of the extract were injected into an Agilent 6890N Gas Chromatograph with an Agilent 5973 inert Mass Selective detector and a BP20 column. The injector was operated at 240° C. with a helium carrier gas with a ramp flow of 1 ml min⁻¹ for 52 min, and then increased to 2.4 ml min⁻¹ for 12 mins. The column temperature was programmed to increase from 40° C. to 166° C. at a rate of 3° C. min⁻¹, followed by an increase of 40° C. min⁻¹ to 270° C. The Mass spectrometer conditions were set to 250° C. for the interface.

The thiols were detected in selected ion monitoring mode, using the ions shown in Table 4.

TABLE 4

Compounds and their selected ions in SIM mode

| Compound | Quantifier | Qualifier |
|---|---|---|
| 3-mercaptohexyl acetate (3MHA) | 116 | 101 |
| 3MHA-D | 118 | 103 |
| 3-mercaptohexan-1-ol (3MH) | 134 | 100 |
| 3MH-D | 102 | 136 |

Quantification of the compounds was carried out by comparing the peak area of the appropriate compound with the peak area of the known concentration of the respective standard.

Results

FIGS. 3 to 12 show the mean, and standard error of the mean, of 3MHA and 3MH levels from the triplicate ferments conducted. All values are in ng l⁻¹.

All P values on these figures indicate the probability that the amount of thiol in the two treatments under consideration is the same, as calculated using a simple t-test (one tailed).

First Set of Ferments.

FIGS. 3 to 8 show the data gathered from the first set of ferments corresponding to single 100% inoculations with the indicated strains and mixed ferment yeast inoculation proportions as detailed in Table 1. These were analysed and quantified using benzenemethanthiol as the internal standard.

FIGS. 3 to 6 show thiol amounts for individual species comparisons. FIGS. 7 and 8 plot all species for either 3MH or 3MHA and reproduce the data provided in FIGS. 3 to 6.

3MHA Production in Mixed Ferments Containing PK-KR1

FIG. 3 shows that the amount of 3MHA produced in the mixed ferment inoculated with VL3 (10%) and PK-KR1 (90%) was substantially elevated when compared to the ferments inoculated with the single species only. The mixed ferment of VL3 (10%) and PK-KR1 (90%) produced approximately three times as much 3MHA than either of the ferments inoculated with the single species alone. This increase in 3MHA production in the mixed ferment was determined to be statistically significantly (P=0.005).

FIG. 3 also shows that there was an increase in 3MHA in mixed ferments inoculated with the reciprocal mix (VL3, 90%+PK-KR1, 10%), albeit not as dramatic but nonetheless significant (P=0.01).

3MHA Production in Mixed Ferments Containing PK-KR2

FIG. 4 shows that the amount of 3MHA produced by all the mixed ferment ratios of VL3 and PK-KR2 were elevated when compared to single ferments of the two species.

3MH Production in Mixed Ferments Containing PK-KR1

FIG. 5 shows that the levels of 3MH were elevated in the mixed ferments inoculated with VL3 and PK-KR1 when compared to ferments inoculated with the single species only.

3MH Production in Mixed Ferments Containing PK-KR2

FIG. 6 shows that the amount of 3MH produced by all the mixed ferment ratios of VL3 and PK-KR2 were elevated when compared to single ferments of the two species.

Overview of Results from the First Set of Ferments

In general, it seems that ferments with certain mixes of the yeast strains of the present invention and a *Saccharomyces* species strain produced an elevated amount of 3MHA and/or 3MH when compared to the ferments with single strains. Certain mixes of VL3 with PK-KR1 and PK-KR2 produced elevated amounts of 3MHA and 3MH.

Second Set of Ferments

In order to determine whether the increase in thiol level observed in the first set of ferments resulted from using different amounts of VL3 in the inoculum, a second set of ferments were carried out examining the effect of different amounts of VL3 on thiol production in single and mixed ferments with PK-KR1.

FIGS. 9 and 10 show the data from the second set of ferments corresponding to the inoculum sizes detailed in Table 2 and mixed ferment inoculation ratios detailed in Table 3. The amount of thiol in these experiments was determined using the deuterated standard.

3MHA Production in Ferments Inoculated with Different Amounts of VL3

FIG. 9 shows that although there was a statistically significant effect of VL3 inoculation size on the amount of thiol produced in single ferments, as determined by a one way ANOVA, P=0.003, no obvious trend was apparent. The values for 100% and 10% are slightly decreased compared with the other amounts (50%, 5%, 1%, 0.5% and 0.1%) which are approximately equal. Accordingly, if there is any effect of inoculum size of VL3 on the amount of 3MHA obtained, it is small.

FIG. 9 also shows that the levels of 3MHA were significantly elevated in ferments inoculated with both VL3 and PK-KR1 at ratios of 100:90, 50:90 and 10:90 compared with single inoculum ferments. Significant differences were determined by a t-test when compared to the amounts of 3MHA produced from ferments inoculated with either 100% VL3 or 0.1% VL3.

Importantly, mixed ferments inoculated with particularly commercially relevant inoculum sizes of VL3 and PK-KR1, demonstrate an elevated level of 3MHA compared with single species ferments. These data corroborate the results from the first set of ferments. Commercially relevant inoculum sizes of VL3 and PK-KR1 may apply to ferments with greater than 5% (above $0.25 \times 10^6$ cells $ml^{-1}$) VL3.

3MH Production in Ferments Inoculated with Different Amounts of VL3

FIG. 10 shows that the effect of varying VL3 inoculum amount on levels of 3MH minors that seen for 3MHA. Although there is a significant effect of inoculum size, as determined by a one-way ANOVA, P=0.03, there is no clear trend. The levels of 3MH obtained from the 100% VL3 ferments are lower than the other inoculum sizes which, again, are relatively constant.

FIG. 10 also shows that the levels of 3MH produced by mixed ferments inoculated with VL3 and PK-KR1 were not elevated when compared with the ferments inoculated with a single species alone.

Overview of Results from the Second Set of Ferments

Any effect of VL3 inoculum size is very small and probably has no overall effect on levels of 3MHA and 3MH in isolation.

Summary of Results

Ferments conducted with a mixture of VL3 and the two *Pichia kluyveri* strains isolated from Kumeu River show elevated amounts of 3MHA and/or 3MH: the magnitude of the increase depends upon the species used and the ratio of the inoculum.

The amount of a commercially available *Saccharomyces cerevisiae* wine strain (VL3) used to inoculate ferments does not account for the amounts of 3MHA and 3MH produced in the ferments with the combined yeast strains.

Example 3

Micro-Fermentation with PK-KR1 and a Range of Commercially Available Wine Yeast Strains in Single and Mixed Cultures The fermentation was carried out using PK-KR1 as prepared in Example 1 and a range of commercially available wine strains (VL3, VIN7, X5, SVG, QA23 and EC118). Fermentation was carried out according to the protocol detailed in Example 2 with the variation that fermentation was conducted at 14° C. rather than at 25° C. (This is within the temperature at which SB is fermented commercially). Thiol extraction and quantification was carried out according to the protocol described in Example 2.

FIG. 11a shows that mixed ferments of 10% VL3 and 90% PK-KR1, 10% VIN7 and 90% PK-KR1 as well as 10% X5 and 90% PK-KR1 produced an elevation of the 3MHA compared with single species ferments. Additional experiments show that although PK-KR1 produced reasonable amounts of 3MHA alone, the sugar decrease in this ferment was minimal indicating that the product may not have a highly desirable flavour.

FIG. 11b shows that the mixed ferments of PK-KR1 with the range of commercially available wine yeast strains did not result in an elevated production of 3MH.

Co-fermentation with PK-KR1 and PK-KR2 with VIN7 were repeated in 5 litre volumes with four replicates (n=4). The inoculation procedures, ratios and thiol analyses were as described above and the results are shown in FIG. 12. Analyses of Variance shows that the treatment (strain/mix of strains used) had an effect on both the levels of 3MHA (F=4.02; P=0.02) and 3MH (F=4.28; P=0.02). The mixtures which included just PK-KR1 and/or PK-KR2 had significantly more 3MH and 3MHA that the other mixtures (P>0.05).

Population Dynamics

To gain a better understanding of these co-ferments with PK-KR1 we monitored the change in frequency of each of the co-fermenting partners through the ferment.

Methods 1 ml samples were aseptically taken every day from the sideport of the fermentation flasks. The samples were plated on YPD (1% yeast extract, 2% peptone, 2% glucose) agar plates in appropriate dilutions and incubated at 30° C. for 24 h before colonies were counted (n~200). For the mixtures with the PK-KR1 a selective medium is not necessary to distinguish the two, since both yeasts have a unique colony morphology that can be distinguished on YPD agar plates.

To monitor the usage of Yeast Available Nitrogen (YAN), glucose and fructose, 1 ml samples were aseptically taken every two days of the ferment. Two test kits were used to determine the amount of YAN: 1° Amino Nitrogen-B1 (Unitech Scientific, California) and Ammonia (Unitech Scientific, California). The sum of both tests yields the total YAN. To determine the amount of D-Glucose and Fructose in a sample the D-Glucose/Fructose Kit (Unitech Scientific, California) was used. All test kits are based on simple enzymatic reactions that were monitored by a UV-spectrophotometer.

For the proline assay a synthetic defined medium consisting of 1.7 g/l Yeast nitrogen base without nitrogen, amino acids and a carbon source (YNB), 200 g/l glucose and 0.45 g/l L-Proline (≥99%; Sigma reagent P0380) was used—this amount of proline emulates the amounts found in a typical grape juice. The medium was inoculated with $2.5 \times 10^6$ yeast cells/ml and the samples were fermented in vessels containing air locks at 14° C. with shaking at 100 rpm. These experiments were repeated but amended in the following ways: the yeast cells were starved of carbon and nitrogen by placing in limiting media for 48 hours to ensure the cellular C and N stores were depleted; the excess $O_2$ in the flasks was purged using solid $CO_2$ (dry ice) which was allowed to sublime in the media; and, treatments were included where no glucose or proline were added to the YNB.

Result

Nutrient Use in the Ferment

The results of the population dynamic experiment are shown in FIG. 13 and indicate that PK-KR1 persisted, and achieved large population sizes, in the co-ferments. Since nitrogen is known to be a limiting essential resource in juice, we sought to monitor the change in nutrients in the single and co-ferments to ascertain which species were utilizing which resources and when. As expected, in the VL3 single ferment YAN decreased within the first four days of fermentation (FIG. 14a) and glucose/fructose amounts decreased over the entire ferment as they were utilized (FIG. 14b). The co-ferment with PK-KR1 shows a time delay of two days for YAN and also glucose/fructose usage. Interestingly not all the YAN and glucose/fructose that VL3 utilizes when alone seems to be used in the co-ferment. However, an intriguing result was observed in the PK-KR1 single ferment. Despite PK-KR1 achieving such large population sizes ($3.5 \times 10^7$ cfu/ml), these data show that the main nitrogen and carbon sources in the grape juice were not utilized. Only 16% of YAN and 11% of glucose/fructose was consumed, yet PK-KR1 achieved large viable population sizes.

Nutrient Source

*S. cerevisiae* is unable to utilize proline under anaerobic conditions (the PutI enzyme in the degradation pathway requires $O_2$ (Ingledew et al. 1987) and the test kit for primary amino nitrogen is not able to detect proline. However, proline is one of the most abundant amino acids in grapes (Ough and Stashak 1974; Spayd and Andersen-Bagge 1996). In order to test the hypothesis that PK-KR1 is able to use proline under ferment conditions we fermented VL3 and PK-KR1 in a synthetic defined medium containing proline as the sole nitrogen source. FIG. 15 shows the population dynamics during these ferments. Unexpectedly, PK-KR1 shows the same growth rate as the previous experiments in grape juice and achieves approximately similar population sizes ($3.5 \times 10^7$ cfu/ml and $2.48 \times 10^7$ cfu/ml). In stark contrast, VL3 shows significantly reduced population sizes across the entire ferment and is unable to even achieve two population doublings. These data concur with previous reports that *S. cerevisiae* is unable to use proline under anaerobic conditions (Ingledew et al. 1987).

Since the amount of glucose and fructose changed little in the grape juice when only PK-KR1 was present, yet high population sizes were achieved, we speculated as to the possible alternate sources of carbon that this organism was assimilating. We conducted a second nutrient use assay. Here we starved the cells in order that they use up their reserves of carbon and nitrogen, arid then placed replicate cultures of PK-KR1 into the same YNB defined medium either with or without proline. This time in order to ensure as little oxygen as possible was present after inoculation a pellet of solid $CO_2$ (dry ice) was added: as this sublimed it purged the flask of air. These were incubated at 28° C. for eight days and the population growth assayed by withdrawing sample (without allowing atmospheric air to enter) and estimating the number of colony forming units per ml. FIG. 16 shows these data. Since there are no sources of carbon or nitrogen, as would be expected no growth of PK-KR1 occurs in the YNB alone; however, the addition of proline to the media allows the population to expand from the initial inoculums of $1.5 \times 10^6$ ml[1] to $2.2 \times 10^7$ by day four. This is approximately 14 times the population size. The inference is that increased biomass was achieved by the assimilation of proline which was used both as a source of energy to carry out catabolic activities (a carbon source) and a source of nitrogen to conduct anabolic biomass build-up.

Although the embodiments of the invention described above were carried out with reference to specific yeast strains and the winemaking fermentation process, the skilled addressee will appreciate that the invention may be carried out in many other forms.

REFERENCES

Brandolini, V., Romano, P., Maietti, A, Caruso, M., Tedeschi, P. and Mazzotta, D., 2002. Automated multiple development method for determination of glycerol produced by wine yeasts. World Journal of Microbiology and Biotechnology 18, 30 481-485.

Clemente-Jimenez, J. M., L. Mingorance-Cazorla, S. Martinez-Rodriguez, F. J. Las Heras-Vazquez, and F. Rodriguez-Vico. 2004. Influence of sequential yeast mixtures on wine fermentation. International Journal of Food Microbiology 98:301-308.

Esteve-Zarzoso, B., Manzanares P., Ramon D and A Querol. 1998. The role of non-*Saccharomyces* yeasts in industrial winemaking. International Microbiology 1: 143-148.

Gachons, C. P. d., T. Tominaga, and D. Dubourdieu. 2000. Measuring the aromatic potential of *Vitis vinifera* L. Cv. Sauvignon Blanc grapes by assaying S-cysteine conjugates, precursors of the volatile thiols responsible for their varietal aroma. Journal of agricultural and food chemistry 48:3387-3391.

Garde-Cerdan, T., and C. Ancin-Azpilicueta. 2006. Contribution of wild yeasts to the formation of volatile compounds in inoculated wine ferments. European Food Research Technology 222:15-25.

Heard, G. M., Fleet, G. H., 1986. Occurrence and growth of yeast species during the fermentation of some Australian wines. Food Technology in Australia 38 (1),22-25.

Heard, G. M., Fleet, G. H., 1988. The effects of temperature and pH on the growth of yeast species during the fermentation of grape juice. Journal of Applied Bacteriology 65,23-28.

Houtman, A. C., Marais, J., Du Plessis, C. S., 1980. Factors affecting the reproducibility of fermentation of grape juice and of the aroma composition of wines: I. Grapes maturity, sugar, inoculum concentration, aeration, juice turbidity and ergosterol. *Vitis* 19, 37-54.

Howell, K. S., Swiegers, J. H., Elsey, G. M., Siebert, T. E., Bartowsky, E. J., Fleet, G. H., Pretoius, I. S., de Banos Lopes, M. A 2004. Variation in 4-mercapto-4-methylpentan-2-one release by *Saccharomyces cerevisiae* commercial wine strains. FEMS Microbiology Letters 240, 125-29.

Howell, K. S., M. Klein, J. H. Swiegers, Y. Hayasaka, G. M. Elsey, G. H. Fleet, P. B. Høj, I. S. Pretorius, and M. A. de Barros Lopes. 2005. Genetic determination of volatile-thiol release by *Saccharomyces cerevisiae* during wine fermentation. Applied and Environmental Microbiology 71:5420-5426.

Ingledew W M, Magnus C A, Sosulski F W (1987) Influence of Oxygen on Proline Utilization During the Wine Fermentation. Am. J. Enol. Vitic. 38, 246-248.

Johnson, L. J., V. Koufopanou, M. R Goddard, R Hetherington, S. M. Schafer, and A. Burt. 2004. Population genetics of the wild yeast *Saccharomyces paradoxus*. Genetics 166: 43-52.

Kurtzman, C. P., and C. J. Robnett. 1998. Identification and phylogeny of ascomycetous yeasts from analysis of nuclear large subunit (26S) ribosomal DNA partial sequences. Antonie Van Leeuwenhoek International Journal of General and Molecula Microbiology 73:331-371.

Kurtzman C P. and. Fell J W 2006 Yeast Systematics and Phylogeny—Chapter 2 Implications of Molecular Identification Methods for Studies in Ecology in Biodiversity and Ecophysiology of Yeasts Carlos Rosa, Gábor Péter (Eds.), Springer.

Lambrechts, M. G., and I. S. Pretorius. 2000. Yeast and its importance to wine aroma—a review. South African Journal for Enology and Viticulture 21:97-129.

Leaw, S, N., Chang, H. C., Sun, H. S., Barton, R, Bouchara, J., Chang, T. C. (2006) Identification of Medically Important Yeast Species by Sequence analysis of the Internal Transcribed Spacer Regions. Journal of Clinical Microbiology. Vol. 4, No 3. pp 693-699.

Lema, C., Garcia-Jares, C., Orriols, I., Angulo, L., 1996. Contribution of *Saccharomyces* and non-*Saccharomyces* populations to the production of some components of Albariño wine aroma. American Journal of Enology and Viticulture 47, 20~216.

Nykänen, L., 1986. Formation and occurrence of flavour compounds in wine and distilled alcoholic beverages. American Journal of Enology and Viticulture 37, 84-96.

Ough C S, Stashak R M (1974) Further Studies on Proline Concentration in Grapes and Wines. Am. J. Enol. Vitic. 25, 7-12.

Ramano, P., C. Fiore, M. Paraggio, M. Caruso, and A Capece. 2003. Function of yeast species and strains in wine flavour. International Journal of Food Microbiology 86: 169-180.

Rapp, A, Versini, G., 1991. Influence of nitrogen compounds in grapes on aroma compounds of wine. In: RANTZ (Ed.), Proceedings of the International Symposium on Nitrogen in Grapes and Wines. American Society for Enology and Viticulture, Davis, Calif., pp. 156-164.

Ribereau-Gayon, P., D. Dubourdieu, B. Doneche, and A. Lonvaud. 2006. Handbook of Enology. 2nd edition. John Wiley & Sons, Chicester, UK.

Rojas, V., J. V. Gil, F. Pinaga, and P. Manzanares. 2003. Acetate ester formation in wine by mixed cultures in laboratory ferments. International Journal of Food Microbiology 86:181-188.

Spayd S E, Andersen-Bagge J (1996) Free Amino Acid Composition of Grape Juice From 12 *Vitis vinifera* Cultivars in Washington. Am. 1. Enol. Vitic. 47, 389-402.

Tominaga, T., A Furrer, R. Henry, and D. Dubourdieu. 1998a. Identification of new volatile thiols in the aroma of *Vilis vinifera* L. var. Sauvignon blanc wines. Flavour and Fragrance Journal 13: 159-162.

Tominaga, T., C. P. d. Gachons, and D. Dubourdieu. 1998b. A new type of flavor precursors in *Vilis vinifera* L. cv. Sauvignon blanc: S-cysteine conjugates. Journal of Agricultural and Food Chemistry 46:5215-5219.

Tominaga, T., M.-L. Murat, and D. Dobourdieu. 1998c. Development of a method for analyzing the voltile thiols involved in the characteristic aroma of wines made from *Vilis vinifera* L. Cv Sauvignon Blanc. Journal of Agricultural and Food Chemistry 46: 1044-1048.

Walsh, P. S., Metzger, D. A, and Higuchi, R. (1991) Chelex® 100 as a medium for simple extraction of DNA for PCR-based typing from forensic material. BioTechniques. Vol 10, No 4. pp 506-511.

White, T. J., T. Bruns, S. Lee, and 1. Taylor. 1990. Amplification and direct sequencing of fungal ribosomal RNA genes for phylogenetics, p. 315-322. In M. A. Innes, D. H. Gelfand, T. T. Sninsky, and T. J. White (ed.), PCR Protocols: a guide to methods and applications. Academic Press, San Diego.

The invention claimed is:

1. A method of fermentation, comprising fermenting a fermentation medium with yeast strains comprising (i) a *P. kluyveri* yeast strain selected from the group consisting of V06/022711, V06/022712, and combinations thereof and (ii) a *Saccharomyces* yeast strain, at a concentration ratio of (i):(ii) of from 10:90 to 90:10.

2. The method of claim 1, wherein the method comprises adding said yeast strains to the fermentation medium.

3. The method of claim 2, wherein the yeast strains (i) and (ii) are added to the fermentation medium simultaneously.

4. The method of claim 1, wherein the method comprises adding a starter culture comprising at least one of the yeast strains (i) and (ii) to the fermentation medium.

5. The method of claim 1, wherein the Saccharomyces strain is selected from the group consisting of VL3, VIN 7, and X5.

6. The method of claim 1, further comprising adding proline to the fermentation medium.

7. The method of claim 1, wherein the yeast strains (i) and (ii) derive one or both of nitrogen and carbon from different sources.

8. The method of claim 1, wherein the fermentation medium is grape juice.

9. The method of claim 1, wherein the method is effective to produce a synergistic increase in at least one thiol in a fermentation product relative to a fermentation product produced by a comparable method but without fermenting a fermentation medium with a *P. kluyveri* yeast strain.

10. The method of claim 9, wherein the thiol is one or both of 3-mercaptohexyl acetate and 3-mercaptohexan-1-ol.

11. The method of claim 10, wherein the fermentation product is an alcoholic beverage.

12. The method of claim 11, wherein the alcoholic beverage is wine.

13. The method of claim 12, wherein the wine is white wine.

14. The method of claim 13, wherein the white wine is sauvignon blanc.

15. The method of claim 10, wherein the method is effective to enhance the flavor of the fermentation product relative to a fermentation product produced by a comparable method but without fermenting a fermentation medium with a *P. kluyveri* yeast strain.

16. The method of claim 1, wherein (i) comprises about 90% of total yeast in the fermentation medium.

17. The method of claim 1, wherein (i) comprises 10% of total yeast in the fermentation medium.

18. The method of claim 1, wherein the concentration ratio of (i):(ii) is 10:90.

19. The method of claim 1, wherein the concentration ratio of (i):(ii) is 50:50.

20. The method of claim 1, wherein the concentration ration of (i):(ii) is 90:10.

* * * * *

SEQUENCE LISTING

```
<160> NUMBER OF SEQ ID NOS: 9

<210> SEQ ID NO 1
<211> LENGTH: 19
<212> TYPE: DNA
<213> ORGANISM: Artificial Sequence
<220> FEATURE:
<223> OTHER INFORMATION: Primer

<400> SEQUENCE: 1
tccgtaggtg aacctgcgg                                                      19

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
tcctccgctt attgatatgc                                                     20

<210> SEQ ID NO 3
<211> LENGTH: 24
```

```
<212> TYPE: DNA
<213> ORGANISM: Artificial Sequence
<220> FEATURE:
<223> OTHER INFORMATION: Primer

<400> SEQUENCE: 3
gcatatcaat aagcggagga aaag                                         24

<210> SEQ ID NO 4
<211> LENGTH: 19
<212> TYPE: DNA
<213> ORGANISM: Artificial Sequence
<220> FEATURE:
<223> OTHER INFORMATION: Primer

<400> SEQUENCE: 4
ggtccgtgtt tcaagacgg                                               19

<210> SEQ ID NO 5
<211> LENGTH: 294
<212> TYPE: DNA
<213> ORGANISM: Pichia kluyveri

<400> SEQUENCE: 5
ttgtaataat accagtcact aagttttaac aaaacaaaac tttcaacaac ggatctcttg    60
gttctcgcat cgatgaagag cgcagcgaaa tgcgatacct agtgtgaatt gcagccatcg   120
tgaatcatcg agttcttgaa cgcacattgc gccccatggt attccatggg catgcctgt   180 ctgagcgtcg tttccttctt gcgcaagcag agttgagaac aggctatgcc tttttcgaaa   240
tggaacgtcg tggacgaagt gaactaaatt tttagcacgc tttggccgcc gaac         294

<210> SEQ ID NO 6
<211> LENGTH: 356
<212> TYPE: DNA
<213> ORGANISM: Pichia kluyveri

<400> SEQUENCE: 6
cacatgcgtg agcgcaccaa acacctaaaa ttgtaatamt accagtcact aagttttaac    60
aaaacaaaac tttcaacaac ggatctcttg gttctcgcat cgatgaagag cgcagcgaaa   120
tgcgatacct agtgtgaatt gcagccatcg tgaatcatcg agttcttgaa cgcacattgc   180
gccccatggt attccatggg catgcctgt ctgagcgtcg tttccttctt gcgcaagcag    240
agttgagaac aggctatgcc tttttcgaaa tggaacgtcg tggacgaagt gaactaaatt   300
tttagcacgc tttggccgcc gaacttttaa ctaagctcga cctcagatca ggtagg       356

<210> SEQ ID NO 7
<211> LENGTH: 367
<212> TYPE: DNA
<213> ORGANISM: Pichia kluyveri

<400> SEQUENCE: 7
tttgaaatct cacctagtgt gcgagttgta aattgcaggt tggagtctcg ggttagacgt    60
gtgtgcaagt cccttggaac agggtgccac tgagggtgag agccccgtat cgtgcatgtc   120
gacacctgtg aggcccttct gacgagtcga gttgtttggg aatgcagctc taagtgggtg   180
gtaaattcca tctaaggcta aatattggcg agagaccgat agcgaacaag tactgtgaag   240
gaaagatgaa aagcactttg aaaagagagt gaaacagcac gtgaaattgt tgaaagggaa   300
gggtattggg ctcgacatgg gatttacgca tcgttgcctc tcgtgggcgg cgctctgggt   360
```

```
ttttcct                                                                367

<210> SEQ ID NO 8
<211> LENGTH: 539
<212> TYPE: DNA
<213> ORGANISM: Pichia kluyveri
<220> FEATURE:
<221> NAME/KEY: misc_feature
<222> LOCATION: (402)..(402)
<223> OTHER INFORMATION: n is a, c, g, or t

<400> SEQUENCE: 8
gatttgaaat ctcacctagt gtgcgagttg taaattgcag gttggagtct cgggttagac      60
gtgtgtgcaa gtcccttgga acagggtgcc actgagggtg agagcccgt agcgtgcatg      120 tcgacacctg tgaggcccct ctgacgagtc gagttgtttg ggaatgcagc tctaagtggg     180
tggtaaattc catctaaggc taaatattgg cgagagaccg atagcaaca agtactgtga      240 aggaaagatg aaaagcactt tgaaaagaga gtgaaacagc acgtgaaatt gttgaaaggg     300
aagggtattg ggctcgacat gggatttacg catcgttgcc tctcgtgggc ggcgctctgg    360 gttttcctg ggccagcatc ggttttcgtt gcaggataag ancaattgga atgtggctcc      420
tcggagtgtt atagcctttt gtagatgctg cgtatgggga ccgagggctg cggcggactc    480
gtttcgtctc ggatgctggc acaacggcgc aataccgccc gtcttgaaac acggaccaa     539

<210> SEQ ID NO 9
<211> LENGTH: 436
<212> TYPE: DNA
<213> ORGANISM: Pichia kluyveri
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 9
gtatangata taaatcacng taatgatcct tccgtaggtg gaacctgcgg aaggatcatt     60
actgtgattt atatcttata cacatgcgtg agcgcaccaa acacctaaaa ttgtaatamt    120
accagtcact aagttttaac aaaacaaaac tttcaacaac ggatctcttg gttctcgcat    180
cgatgaagag cgcagcgaaa tgcgatacct agtgtgaatt gcagccatcg tgaatcatcg    240
agttcttgaa cgcacattgc gccccatggt attccatggg gcatgcctgt ctgagcgtcg    300
tttccttctt gcgcaagcag agttgagaac aggctatgcc tttttcgaaa tggaamgtcg    360
tggacgaagg tgaactaaat ttttagcacg ctttggccgc cgaactttaa ctaagctcga    420
cctcagatca ggtagg                                                    436
```